United States Patent [19]

Chapin et al.

[11] 4,370,319

[45] Jan. 25, 1983

[54] SKIN CONDITIONING COMPOSITIONS

[75] Inventors: Carole N. Chapin; Gary R. Kelm; David L. Shelton, all of Cincinnati, Ohio

[73] Assignee: The Procter & Gamble Company, Cincinnati, Ohio

[21] Appl. No.: 245,827

[22] Filed: Mar. 20, 1981

Related U.S. Application Data

[63] Continuation of Ser. No. 161,173, Jun. 19, 1980, abandoned.

[51] Int. Cl.³ .................. A61K 31/695; A61K 47/00
[52] U.S. Cl. .................................... 424/184; 424/170; 424/172; 424/365
[58] Field of Search .................... 424/184, 170, 172

[56] References Cited

U.S. PATENT DOCUMENTS

| | | | |
|---|---|---|---|
| Re. 29,814 | 10/1978 | Snyder | 424/81 |
| 3,681,412 | 8/1972 | Betzing | 260/403 |
| 3,875,196 | 4/1975 | Meguro et al. | 260/403 |
| 3,959,491 | 5/1976 | Young et al. | 424/359 |
| 4,104,403 | 8/1978 | Barker et al. | 424/365 |
| 4,160,773 | 7/1979 | Eibl et al. | 260/403 |

FOREIGN PATENT DOCUMENTS 14509  8/1980  European Pat. Off. .

OTHER PUBLICATIONS

Scher Chemicals, Inc., Technical Bulletons SG0202, 0208 and 0211, available to the public approximately Jan., 1977.

*Primary Examiner*—Donald B. Moyer
*Attorney, Agent, or Firm*—Douglas C. Mohl; Richard C. Witte; John V. Gorman

[57] ABSTRACT

Skin conditioning compositions comprising an alkali metal phosphoric acid ester salt of a partial glyceride, silicone fluid, a long chain alkyl ester of a fatty acid, an emollient material, an emulsifier and water. The phosphated glyceride and the dimethicone fluid serve to provide greater retention of the conditioning composition on the skin.

11 Claims, No Drawings

SKIN CONDITIONING COMPOSITIONS

This is a continuation of application Ser. No. 161,173, filed June 19, 1980 now abandoned.

TECHNICAL FIELD

The present invention relates to novel skin conditioning compositions which are very retentive on skin thereby reducing moisture loss from the skin surface.

The treatment of human skin with various agents has been undertaken for many years with the goal being to keep the skin in a smooth and supple condition. Skin has the tendency to dry out when exposed to conditions of low humidity or to extended periods in a detergent solution. From a biochemical standpoint, dryness is a measure of the water content of the skin. Under normal conditions, the water content and vapor pressure of the epidermis are higher than those of the surrounding air with consequent evaporation of water from the skin surface. Skin becomes dry because of excessive loss of water from the surface and the subsequent loss of water from the stratum corneum.

Continuous and prolonged immersion in soap or detergent solutions may contribute to dryness of the stratum corneum. The reason for this is that the surfactant medium promotes dissolution of the skin surface lipids, the horny layer lipids, and the dissolution of the hygroscopic water-soluble components in the corneum.

BACKGROUND ART

To alleviate the aforementioned conditions, emollient creams as described in Sagarin, *Cosmetics Science and Technology*, 2nd Edition, Vol. 1, Wiley Interscience (1972) have been recommended for application to the skin. The emollient materials probably increase the state of hydration of the corneous layer of the skin by altering the rate of diffusion of water from the lower epidermal and dermal layers, the rate of evaporation of water from the skin's surface, and the ability of the corneous layer to hold moisture.

Numerous other references have disclosed the use of a wide variety of materials for alleviating the problems of dry skin. Included among such references are those in which alkali metal phosphoric acid ester salts of partial glycerides and dimethicone fluids of the type used in the compositions of the present invention have been disclosed. U.S. Pat. No. 4,104,403, Aug. 1, 1978 to Barker et al discloses water in oil emulsions containing phosphated mono- and/or di glycerides and an aluminum or calcium stearate. U.S. Pat. No. Re. 29,814, Oct. 24, 1978, to Synder discloses compositions which contain a dimethicone fluid. However, neither of these references teach or suggest combining these materials in compositions as set forth herein. References which disclose compositions containing long chain esters of the type used in the present compositions include U.S. Pat. No. 3,959,491, May 25, 1976 to Young et al and *Technical Bulletins* S.G. 0202 and S.G. 0211 distributed by Scher Chemicals, Inc. These references, however, do not suggest compositions containing a glyceride and a dimethicone.

It is an object of the present invention to provide compositions which are retained better on skin.

It is a further object of the present invention to provide a better method for conditioning skin.

These and other objects will become apparent from the detailed description which follows.

DISCLOSURE OF THE INVENTION

The present invention relates to superior skin conditioning compositions comprising from about 0.1% to about 5% of an alkali metal phosphoric acid ester salt of a partial glyceride, from about 0.1% to about 5% of a silicone fluid, from about 0.05% to about 8% of an emulsifier, from about 0.1% to about 16% of a long chain alkyl ester of a fatty acid, an emollient in an amount such that the amount of long chain alkyl ester and emollient is from about 0.2% to about 25%, and the remainder water.

DETAILED DESCRIPTION OF THE INVENTION

It has been discovered that compositions comprising the above generally described components are retained very well on skin. The compositions, in addition to their ability to be retained, possess good cosmetics. The individual components are described in detail below.

ALKALI METAL PHOSPHORIC ACID ESTER SALT

The phosphated glycerides contemplated herein are well known. They are the alkali metal phosphoric acid ester salts of partial glycerides, i.e., the ester salts of mono- and di-glycerides.

The phosphated mono- and di-glycerides may be prepared in a number of ways. Generally, a derivative of phosphorus, such as phosphorus pentoxide, a polyphosphoric acid, or anhydrous phosphoric acid is reacted with the mono- or di-glyceride, or mixtures thereof, the fatty acid ester moiety or moieties of the glyceride being saturated and/or unsaturated (mono- or di-).

These and other methods of preparing the phosphated mono- and di-glycerides within the purview of the present invention are taught in the art. Illustrative literature is the following: U.S. Pat. Nos. 2,026,785, 2,177,983, 2,177,984. 3,248,229, and 3,875,196; British Pat. No. 1,174,789; Japanese Patent Publication No. 14322/68; Geman Pat. No. 719,830; Chem. Ber. 71, 1071 (1938); and Chem. Ber. 71, 1505 (1938).

In U.S. Pat. No. 3,875,196 for instance, phosphoric acid esters of mono- or di-glycerides are prepared by reacting a mono- or di-glyceride ester of stearic acid, myristic acid, palmitic acid, palmitoleic acid, or a mixed acid ester thereof, with a polyphosphoric acid. The polyphosphoric acid is prepared by heating phosphoric acid or by heat treating phosphoric acid which phosphorus pentoxide.

According to U.S. Pat. No. 3,875,196, the corresponding ester salts of the phosphated mono- and di-glycerides are prepared by meutralizing the glyceride ester. For example, glyceride ester crystals recovered from the reactions of a polyphosphoric acid and, say, a monoglyceride are neutralized with an aqueous sodium hydroxide solution and the monosodium phosphoric acid ester of the monoglyceride is recovered.

In the present invention, one may employ mixtures of these phosphated monoglycerides, mixtures of the phosphated diglycerides, or mixtures of both. Of course, the fatty acid ester moieties in a diglyceride may be the same or different. For example, the fatty acid ester moieties of the diglyceride, such as those derived from $C_{11}-C_{18}$ saturated, mono-unsaturated or di-unsaturated fatty acids, may be the same or different.

The phosphated mono- and/or di-glyceride is present, according to the instant discovery, in the concentration of about 0.1 to about 5 percent by weight, preferably about 0.5 to about 3 percent, based upon the total weight of the composition.

NON-VOLATILE SILICONE FLUID

The non-volatile silicone fluid useful in the present invention may be either a polyalkyl siloxane or a polyalkylaryl siloxane.

The essentially non-volatile polyalkyl siloxanes that may be used include, for example, polydimethyl siloxanes with viscosities ranging from about 10 to 100,000 centistokes at 25° C. These siloxanes are available, for example, from the General Electric Company as the Vicasil series and from Dow Corning as the Dow Corning 200 series.

The essentially non-volatile polyalkylaryl siloxanes that may be used include, for example, polymethylphenylsiloxanes having viscosities of about 15 to 65 centistokes at 25° C. These siloxanes are available, for example, from the General Electric Company as SF 1075 methyl phenyl fluid or from Dow Corning as 556 Cosmetic Grade Fluid.

The non-volatile silicone is present in the compositions herein at a level of from about 0.1% to about 5%, preferably 0.5% to about 3%.

Emulsifier

An emulsifier in an amount of from about 0.05% to about 8%, preferably from about 0.25% to about 5.0%, is included in the compositions of the present invention to emulsify the oil components. The emulsifier is selected from the group consisting of polyethoxylated fatty acids having less than about 30 moles of ethylene oxide per mole of fatty acid, ethoxylated esters, unethoxylated sugar esters, polyoxyethylene fatty ether phosphates, fatty acid amides, phospholipids, polypropoxylated fatty ethers, acyl lactylates, polyethoxylated poly (oxypropylene) glycols, polypropoxylated poly (oxyethylene) glycols, poly (oxyethylene) poly (oxypropylene) ethylene diamines, soaps and mixtures thereof.

Examples of such emulsifiers include polyoxyethylene (8) stearate, myristyl ethoxy (3) myristate, myristyl ethoxy (3) palmitate, methyl glucoside sequistearate, sucrose distearate, surcrose laurate, sorbitan monolaurate, polyoxyethylene (3) oleyl ether phosphate, polyoxyethylene (10) oleyl ether phosphate, lauric diethanolamide, stearic monoethanolamide, lecithin, lanolin alcohol propoxylates, sodium stearoyl-2-lactylte, calcium stearoyl-2-lactylate and the Pluronics offered by BASF Wyandotte. Soaps are acceptable emulsifiers, particularly if the concentration of the soap is less than about 1.6%. The soaps may be formed in situ in processing the composition and are preferably alkali metal or triethanolamine salts of long chain fatty acids. Such soaps include sodium stearate, triethanolamine stearate and the similar salts of lanolin fatty acids.

Preferred emulsifiers are the polyethoxylated fatty acids having less than about 30 moles of ethylene oxide per mole of fatty acid, ethoxylated esters and the acyl lactylates.

Long Chain Alkyl Ester of a Fatty Acid

The ester component of the compositions of the present invention has the structural formula

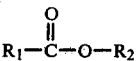

wherein $R_1$ and $R_2$ are both straight chain alkyls having from about 6 to about 22 carbon atoms and the total number of carbon atoms in the ester is at least about 24. Examples of such esters include lauryl laurate, lauryl myristate, myristyl myristate, behenyl caprate, cetearyl palmitate, behenyl stearate. Esters having a total number of carbon atoms in excess of about 28 are preferred. Cetearyl palmitate and cetyl stearate are most preferred esters. There are, of course, many other esters which meet the above described requirements and are suitable for use in the present compositions.

Each chain of the ester, as indicated above, may contain from about 6 to about 22 carbon atoms while the total number must be at least about 24. Thus esters having substantially unequal numbers of carbon atoms in the two chains are suitable for use in the present compositions. Chains of approximately equal length are, however, preferred.

The level of the above esters used in the present compositions is from about 0.1% to about 16% of the total composition, preferably from about 1% to about 8%.

The combination of the esters with the other oil phase components is important to the performance of the compositions of the present invention. Given below are preferred minimum and maximum levels for certain of the esters expressed as a percentage of the oil phase.

| CARBON CHAIN LENGTH | MINIMUM % | MAXIMUM % |
| --- | --- | --- |
| $C_{24}$ | 64 | >64 |
| $C_{26}$ | 21 | >64 |
| $C_{28}$ | 9.9 | >64 |
| $C_{30}$ | 6.0 | >64 |
| $C_{32}$ | 4.2 | >64 |
| $C_{34}$ | 3.2 | 35 |
| $C_{36}$ | 2.6 | 23.9 |
| $C_{38}$ | 2.3 | 20.0 |
| $C_{40}$ | 2.0 | 18.2 |
| $C_{42}$ | 1.8 | 17.2 |
| $C_{44}$ | 1.7 | 16.6 |

Emollient Material

The present compositions, in addition to the above described esters, contain an emollient material in an amount such that the amount of ester plus emollient is from about 0.2% to about 25% of the total composition, preferably from about 4% to about 18%. One function of the emollient is to ensure that the ester is plasticized sufficiently to allow it to be in a film-like state on the skin. The emollient in the present compositions is selected from the group consisting of fatty alcohols, esters having fewer than about 24 total carbon atoms (e.g. isopropyl palmitate), branched chain esters having greater than about 24 total carbon atoms (e.g. cetearyl octonate), squalane, liquid or solid paraffins, mixtures of fatty acids and squalane, mixtures of fatty acids and liquid or solid paraffins and mixtures thereof. The aforementioned esters, those having fewer than 24 carbon atoms or branched and having more than 24 carbon atoms, if used as an emollient should preferably be used in an mount equal to about a third of the long chain ester.

The particular emollient selected depends in part on the particular ester selected since proper placticization, as indicated above, is desied. The emollient for the esters having more than 28 carbon atoms is preferably selected from the group consisting of squalane, liquid or solid paraffins and mixtures of fatty alcohols with squalane or paraffins.

Typical fatty alcohols and fatty acids useful in the present compositions include those having from 12–22 carbon atoms such as cetyl alcohol, myristyl alcohol, stearyl alcohol, stearic acid and palmitic acid. Paraffins include, for example, mineral oil, petrolatum and paraffin wax.

Water

It is preferred that distilled water be used in the present compositions.

OPTIONAL COMPONENTS

Oil Phase Components

In addition to the phosphated glyceride, silicone fluid, long chain esters, emollients and emulsifiers described previously, the oil phase of the present compositions may contain a variety of materials including:

(a) Esters not meeting the requirements for the long chain ester and not present as an emollient, supra, such as oleyl oleate, isostearyl isostearate, isopropyl lanolate, isopropyl myristate, butyl stearate, myristyl lactate and 2-ethyl hexyl palmitate;

(b) Oils such as castor oil, jojoba oil, cottonseed oil, peanut oil and sesame oil;

(c) Waxes such as ceresin wax, carnuba wax, beeswax and castor wax;

(d) Lanolin, its derivatives and components such as acetylated lanolin, lanolin alcohols and lanolin fatty acids. Lanolin fatty acids are described in U.S. Pat. No. Re. 29,814, Oct. 24, 1978 to W. E. Snyder incorporated herein by reference.

(e) Polyalkylenes such as hydrogenated polyisobutene and polyethylene; and (f) Sterols such as cholesterol and phytosterol.

These optional oil phase materials may comprise up to about 80% of the oil phase, preferably up to about 35%. When used at these levels, the optional components do not impair the occlusive nature of the compositions and add to the composition's total cosmetic performance.

Water Phase Components

The water phase of the compositions may contain many different materials including:

(a) Humectants, such as sorbitol, glycerine, propylene glycol, alkoxylated glucose and hexanetriol at a level of from about 1% to about 20%.

(b) Thickening agents such as carboxyvinyl polymers, ethyl cellulose, polyvinyl alcohol, carboxymethyl cellulose, vegetable gums and clays such as Veegum ® (magnesium aluminum silicate, R. T. Vanderbilt, Inc.) at a level of from about 0.01% to about 6%;

(c) Proteins and polypeptides at a level of from about 0.1% to about 3%;

(d) Preservatives such as the methyl, ethyl, propyl and butyl esters of hydroxybenzoic acid (Parabens-Mallinckrodt Chemical Corporation) EDTA and imidazolidinyl urea (Germall 115-Sutton Laboratories) at a level of from about 0.2% to about 2.5%; and (e) An alkaline agent such as sodium hydroxide to neutralize, if desired, part of the fatty acids or thickener which may be present.

All of the percentages of these additional water phase components are of the total composition.

The present compositions may also contain agents suitable for aesthetic purposes such as perfumes and dyes. These agents may be used in amounts sufficient to achieve the desired fragrance and color (e.g. from about 0.05% to about 1%).

The compositions of the present invention are preferably substantially free of materials which adversely affect their performance. Therefore, such things as polyethylene glycols are preferably present only at levels below about 1% of the total composition.

The pH of the present compositions is preferably in the range of about 4.5–9.0.

METHOD OF MANUFACTURE

The compositions of the present invention generally have a lotion consistency and may be in the form of oil-in-water or water-in-oil emulsions with the former being preferred because of their more pleasing cosmetic properties.

The compositions of the present invention are preferably made by;

(A) preparing the oil phase;

(B) preparing the water phase; and (C) adding the oil phase to the water phase.

Step (A) is carried out by heating the oil phase materials to a temperature of about 75° C. to about 100° C. Step (B) is carried out by heating the water phase materials to a temperature about the same as that of the oil phase. The emulsion is formed by slowly adding the oil phase prepared in step (A) to the water phase prepared in step (B) with stirring. Other ingredients may be added to the phase in which they are soluble prior to the mixing of the two phases or added directly to the mixed water and oil phases.

INDUSTRIAL APPLICABILITY

The compositions of the present invention are useful in the skin care field generally. They are used in an amount sufficient to meet the individual user's needs and desires.

The following examples further describe and demonstrate the preferred embodiments within the scope of the present invention. Said examples are given solely for the purpose of illustration and are not to be construed as limitations of the present invention, as many variations thereof are possible without departing from the spirit and scope thereof. Unless otherwise indicated, all percentages herein are by weight.

All of the examples are shown as an oil phase and a water phase with the percentages being those of the total composition.

EXAMPLE I

The following composition is exemplary of the present invention:

| COMPONENTS | WT % |
| --- | --- |
| Oil Phase | |
| Petrolatum | 0.5 |
| Cetearyl Palmitate | 1.0 |
| Emphos F-27-85 (hydrogenated vegetable glycerides phosphate)[1] | 0.5 |
| Cetyl Alcohol | 3.0 |
| Amerlate WFA ® (lanolin fatty acids)[2] | 0.5 |
| Stearic Acid | 0.75 |
| Pationic SSL ® (sodium stearoyl-2- | 0.50 |

-continued

| COMPONENTS | WT % |
|---|---|
| lactylate)[3] | |
| MEP-3 (myristyl ethoxy (3) palmitate)[4] | 1.25 |
| Dimethicone[5] 350 Centistoke viscosity at 25° C. | 0.50 |
| Water Phase | |
| Distilled Water | 87.08 |
| NaOH | 0.46 |
| Glycerin | 3.00 |
| Carbopol 934[6] (Carboxy vinyl polymer) | 0.15 |
| Methyl Paraben[5] | 0.20 |
| Propyl Paraben[5] | 0.10 |
| EDTA 4Na | 0.10 |
| Germall 115[7] (imidazolidinyl urea) | 0.10 |
| TiO$_2$ | 0.10 |
| Perfume | 0.01 |

[1]Supplied by Witco Chemical Company. The vegetable glycerides are from cottonseed oil.
[2]Supplied by Amerchol, a unit of CPC International, Inc.
[3]Supplied by Patco Cosmetic Products.
[4]Supplied by Scher Chemicals, Inc.
[5]Supplied by Mallickrodt Chemical Corporation.
[6]Supplied by B.F. Goodrich Co.
[7]Supplied by Sutton Laboratories.

EXAMPLE II

Another typical skin conditioning composition of the present invention has the following formula

| COMPONENTS | WT % |
|---|---|
| Oil Phase | |
| Petrolatum | 0.5 |
| Cetearyl Palmitate | 1.0 |
| Emphos F-27-85 (hydrogenated vegetable glycerides phosphate)[1] | 0.5 |
| Cetyl Alcohol | 3.0 |
| Amerlate WFA ® (lanolin fatty acids)[2] | 0.5 |
| Stearic Acid | 0.5 |
| Pationic SSL ® (sodium stearoyl-2-lactylate)[3] | 0.75 |
| MEP-3 (myristyl ethoxy (3) palmitate)[4] | 1.25 |
| Dimethicone[5] 100 Centistoke viscosity at 25° C. | 0.50 |
| Water Phase | |
| Distilled Water | 85.85 |
| Glycerin | 4.00 |
| Xanthan Gum | 0.30 |
| Methyl Paraben[5] | 0.25 |
| Propyl Paraben[5] | 0.10 |
| EDTA 4Na | 0.10 |
| TiO$_2$ | 0.20 |
| Perfume | 0.20 |

[1]Supplied by Witco Chemical Company. The vegetable glycerides are from cottonseed oil.
[2]Supplied by Amerchol, a unit of CPC International, Inc.
[3]Supplied by Patco Cosmetic Products.
[4]Supplied by Scher Chemicals, Inc.
[5]Supplied by Mallickrodt Chemical Corporation.

EXAMPLE III

The preceding compositions are prepared following the outline below.

1. Oil phase ingredients are placed in a suitable container and heated to 165° F. (73.9° C.).
2. When completely melted they are thoroughly mixed.
3. The water phase ingredients, with the exception of perfume, neutralizing agents (NaOH, TEA, etc.), and pigments (TiO$_2$) are also heated, in a separate container, to 165° F., with mechanical agitation.
4. When both phases are up to the proper temperature, the oil phase is added to the water phase with continued agitation.
5. If the formula contains a neutralizing agent, it is added at this time.
6. After the emulsion has been formed, the preservatives and pigment (if present in the formula) are added.
7. Mixing at moderate shear is continued for 20 minutes.
8. Temperature is lowered, with continued agitation, to 120° F., at which point the perfume is added.
9. After a 10 minute period of mixing, to incorporate the perfume, the mixture is cooled to 80° F. and packed into containers.

What is claimed is:

1. A skin conditioning composition comprising:
   (A) from about 0.1% to about 5% of an alkali metal phosphoric acid ester of a glyceride selected from the group consisting of a monoglyceride, a diglyceride and mixtures thereof.
   (B) from about 0.1% to about 5% of a non-volatile silicone fluid.
   (C) from about 0.1% to about 16% of an ester, or mixtures thereof, having the structural formula

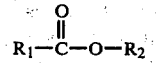

wherein R$_1$ and R$_2$ are both straight chain alkyls having from about 6 to about 22 carbon atoms and the total number of carbon atoms in the ester is at least about 24;
   (D) an emollient selected from the group consisting of fatty alcohols, esters having fewer than about 24 carbon atoms, branched chain esters having greater than about 24 total carbon atoms, squalane, liquid or solid paraffins, mixtures of fatty acids and squalane, mixtures of fatty acids and liquid or solid paraffins and mixtures thereof in an amount such that the amount of ester plus emollient is from about 0.2% to about 25%;
   (E) from about 0.05% to about 8% of an emulsifier selected from the group consisting of polyethoxylated fatty acids having less than about 30 moles of ethylene oxide per mole of fatty acid, ethoxylated esters, unethoxylated sugar esters, polyoxyethylene fatty ether phosphates, fatty acid amides, phospholipids, polypropoxylated fatty ethers, acyl lactylate salts, polyethoxylated poly (oxypropylene) glycols, polypropoxylated poly(oxyethylene) glycols, poly (oxyethylene) poly (oxypropylene) ethylene diamines, soaps, provided the level of soap is less than about 1.6%, and mixtures thereof; and
   (F) water.

2. A skin conditioning composition according to claim 1 wherein the phosphated glyceride is a monoglyceride and the silicone fluid is a polydimethyl siloxane having a viscosity of from about 10 to about 100,000 centistokes at 25° C.

3. A skin conditioning composition according to claim 2 wherein the ester is present at a level of from about 1% to about 8%, the total number of carbon atoms in the ester is in excess of about 28 and the emollient is selected from the group consisting of squalane, liquid or solid paraffins, mixtures of fatty alcohols and squalane and mixtures of fatty alcohols and liquid or solid paraffins.

4. A skin conditioning composition according to claim 3 wherein the emulsifier is selected from the group consisting of polyethoxylated fatty acids having less than about 30 moles of ethylene oxide per mole of fatty acid ethoxylated esters and acryl lactylates.

5. A skin conditioning composition according to claim 4 wherein the emulsifier is present at a level of 0.25% to about 5.0%.

6. A skin conditioning composition according to claim 5 which in addition contains from about 1% to about 20% of a humectant.

7. A skin conditioning composition according to claim 6 which in addition contains additional oil phase components at a level of up to about 80% of the total level of oil phase components.

8. A skin conditioning composition according to claim 7 wherein the ester is selected from the group consisting of cetearyl palmitate and cetyl stearate, the phosphated glyceride is a hydrogenated vegetable glycerides phosphate and the polydimethyl siloxane has a viscosity of about 350 centistokes at 25° C.

9. A skin conditioning composition according to claim 8 which in addition contains a thickening agent.

10. A skin conditioning composition according to claim 9 which is in the form of an oil-in-water emulsion.

11. A method of conditioning skin comprising applying to the skin a sufficient amount of the composition according to claim 1.

* * * * *

UNITED STATES PATENT OFFICE
CERTIFICATE OF CORRECTION

PATENT NO. : 4,370,319
DATED : Jan. 25, 1983
INVENTOR(S) : Carole N. Chapin; Gary R. Kelm; David L. Shelton It is certified that error appears in the above-identified patent and that said Letters Patent are hereby corrected as shown below:

Column 2, line 51, "which" should read --with--;

Column 3, line 47, "surcrose" should read --sucrose--;

Column 5, line 1, "desied." should read --desired.--;

Column 9, line 2, "acryl" should read --acyl--.

Signed and Sealed this

Thirty-first Day of May 1983

[SEAL]

Attest:

DONALD J. QUIGG

Attesting Officer

Acting Commissioner of Patents and Trademarks